United States Patent [19]

Beachey et al.

[11] Patent Number: 4,695,562

[45] Date of Patent: * Sep. 22, 1987

[54] SYNTHETIC PEPTIDE COMPOUNDS

[75] Inventors: Edwin H. Beachey, Memphis, Tenn.; Andre Tartar, Vitry-en-Artois, France; Helene Gras-Masse, Hem, France; Michel Jolivet, Issy-les-Moulineaux, France; Francoise Audibert, Neuilly S/Seine, France; Louis Chedid, Paris, France

[73] Assignee: Univ. of Tennessee Research Corp., Knoxville, Tenn.

[*] Notice: The portion of the term of this patent subsequent to Jun. 12, 2001 has been disclaimed.

[21] Appl. No.: 808,214

[22] Filed: Dec. 11, 1985

Related U.S. Application Data

[63] Continuation of Ser. No. 597,272, Apr. 6, 1984, abandoned, which is a continuation-in-part of Ser. No. 402,355, Jul. 27, 1982, Pat. No. 4,454,121.

[51] Int. Cl.$^4$ .................. A61K 37/02; C07K 7/06; C07K 7/08; C07K 7/10
[52] U.S. Cl. .................................. 514/13; 514/14; 514/15; 530/326; 530/327; 530/328
[58] Field of Search .................. 514/12, 13, 14, 15; 530/326, 327, 328

[56] References Cited

U.S. PATENT DOCUMENTS 4,454,121 6/1984 Beachey ........................... 514/12

Primary Examiner—Delbert R. Phillips
Attorney, Agent, or Firm—Weiser & Stapler

[57] ABSTRACT

Peptide fragment of M protein of *S. pyrogenes* elecit opsonic antibodies which are type-specific for type 24 streptococci.

20 Claims, 5 Drawing Figures

SYNTHETIC PEPTIDE COMPOUNDS

This application is a continuation of application Ser. No. 597,272, filed Apr. 6, 1984, now abandoned, which in turn is a continuation-in-part of Ser. No. 402,355, filed July 27, 1982, now U.S. Pat. No. 4,454,121.

This invention relates to peptide fragments of the M protein of *S. pyogenes*. More particularly, the invention relates to small synthetic immunogenic peptides which are able to elicit opsonic antibodies which are type-specific for type 24 streptococci and which are not serologically cross-reactive with tissue antigens of the human or the host heart.

The invention further relates to haptens which, when linked to a suitable carrier, elicit high titers of type specific opsonic and bactericidal antibodies in rabbits.

The invention further relates to the conjugates of these haptens with appropriate carriers which evoke immune responses which are type specific for type 24 streptococci, and which are not serologically cross-reactive with tissue antigens of the human or host heart.

The invention further relates to the biologically active compositions which comprise the peptide fragments and a biologically acceptable carrier and which are immunogenic with respect to *Streptococcus pyogenes*.

The invention further relates to the method for controlling streptococcal infections in a mammal which comprises administering the biologically active compositions to said mammal.

The invention further relates to homopolymers of peptide fragments of the M protein of *S. pyogenes*.

For over one-half century, attempts have been made to develop safe and effective vaccines against strains of group A streptococci that give rise to rheumatic fever and rheumatic heart desease (Lancefield, R. C, J. Immunol., 89, 307 (1962) and Stollerman, G. H., *Rheumatic Fever and Streptococcal Infection*, Grune and Stra Hon, New York, 1975). Most of these efforts have been frustrated by severe toxic reactions to almost any streptococcal product introduced into the human host. Some of these products have been shown to give rise to antibodies that cross react with host tissues, especially the heart (Kaplan, M. H. and Meyersian, H., Lancet, I, 706 (1962) and Zabriskie, J. B. and Freimer, E. H., J, Exp. Med., 124, 661 (1966)). Although it has long been established that the M protein on the surface of group A streptococci contains the protective antigen (s) of these organisms, the fear has been that the isolated M protein may be associated with potentially harmful tissue cross-reactive antigens that give rise to, rather than prevent, rheumatic fever. This fear has been perpetuated by the finding that certain rheumatogenic streptococci produce M proteins that are closely associated with a heart cross-reactive antigen (Kaplan, M. H., J. Immunol., 90, 595 (1963)). Indeed recently it has been established that one of the M protein molecules contains, within its covalent structure an epitope that ellicits a protective anti-streptococcal antibody that also cross-reacts with a sarcolemmal protein of human heart tissue (Dale, J. B. and Beachey, E. H., J, Exp. Med., 156, 1165 (1982)).

Recently Audibert et al. actively immunized laboratory animals against diphtheria toxin using a chemically synthesized oligopeptide (Audibert, F. et al., Nature 289, 593–594 (1981)). This work does not show, however, that a synthetic peptide antigen can raise antibodies which promote phagocytosis and killing of a bacterial pathogen.

U.S. Pat. No. 4,284,537, to E. Beachey, issued Aug. 18, 1981, disclosed the amino acid sequence of two peptide fragments derived from M protein. It also disclosed that each of these natural fragments, when covalently linked to a carrier such as polylysine, was able to elicit type-specific opsonic antibodies effective against *Streptococcus pyogenes*. Each of these fragments was a natural extract, and each contained 35 amino acids.

The above-referred to patent application (Ser. No. 402,355) teaches and describes inter alia, a synthetic peptide (S-CB7) and that one of the protective determinants is located in a specific fragment of S-CB7 of type 24 M protein which contains only twelve amino acid residues (S-CB7(18-29)). S-CB7, as described, differs from the native CB-7 fragment in that the COOH-terminal residue of S-CB7 is methionine, in contrast to homoserine. The specification also teaches and describes covalently linked conjugates of S-CB7 and appropriate hapten carriers, natural, like BSA or OVA or synthetic, like polylysine. Further details about this work have been published in Nature on July 30, 1981, by Beachey et al., 292, pages 457–459.

U.S. application Ser. No. 503,272 entitled Synthetic Polypeptide Fragments, to Edwin H. Beachey, filed June 9, 1983, discloses the amino acid sequence of three peptide fragments CB3, CB4, and CB5, and 35 and 37 amino acid sequences which contain antigenic determinants corresponding to the antigenic determinants contained in CB3-CB7. It also disclosed that these fragments, when covalently linked to a carrier such as polylysine, are able to elicit type-specific opsonic antibodies effective against *Streptococcus pyogenes*.

Notwithstanding these advances, there remains a serious need, as yet unfilled, to determine precisely the minimal structure of the M protein molecule required to evoke protective immunity without causing tissue cross-reactive adverse reactions. The problem has been described by Hasty et. al, in the J. Exp. Med., Vol. 155, page 1010, April 1982. Another attempt in predicting protein antigenic determinants from amino sequences (including the streptococcal M protein) has been published by Hopp et. al. in the Proc. Natl. Acad. Sci. USA, Vol. 78, No. 6, pages 3824–28, June 1981. The present invention marks another forward step and provides another advance in the medical sciences, particularly in the control of streptococcal infections.

Accordingly, it is a primary object of the invention to provide small synthetic peptide fragments of *S. pyogenes* which are able to inhibit opsonic antibodies obtained from a mammal which has been immunized with uncleaved pep M24 molecules.

It is also an object of the invention to provide peptide fragments which are useful as haptens which, when linked to a suitable carrier, are useful to evoke high titers of type specific opsonic and bactericidal antibodies.

Another object of the invention is the production of biologically active compositions which are immunogenic with respect to *S. pyogenes*.

Another object of the invention is to provide for a method of controlling streptococcal infections in a mammal.

Other worthwhile objects will become apparent from the disclosure herein. Other features and advantages of the invention will appear from the examples which follow and by referring to the appended drawings in which.

Figure 1:
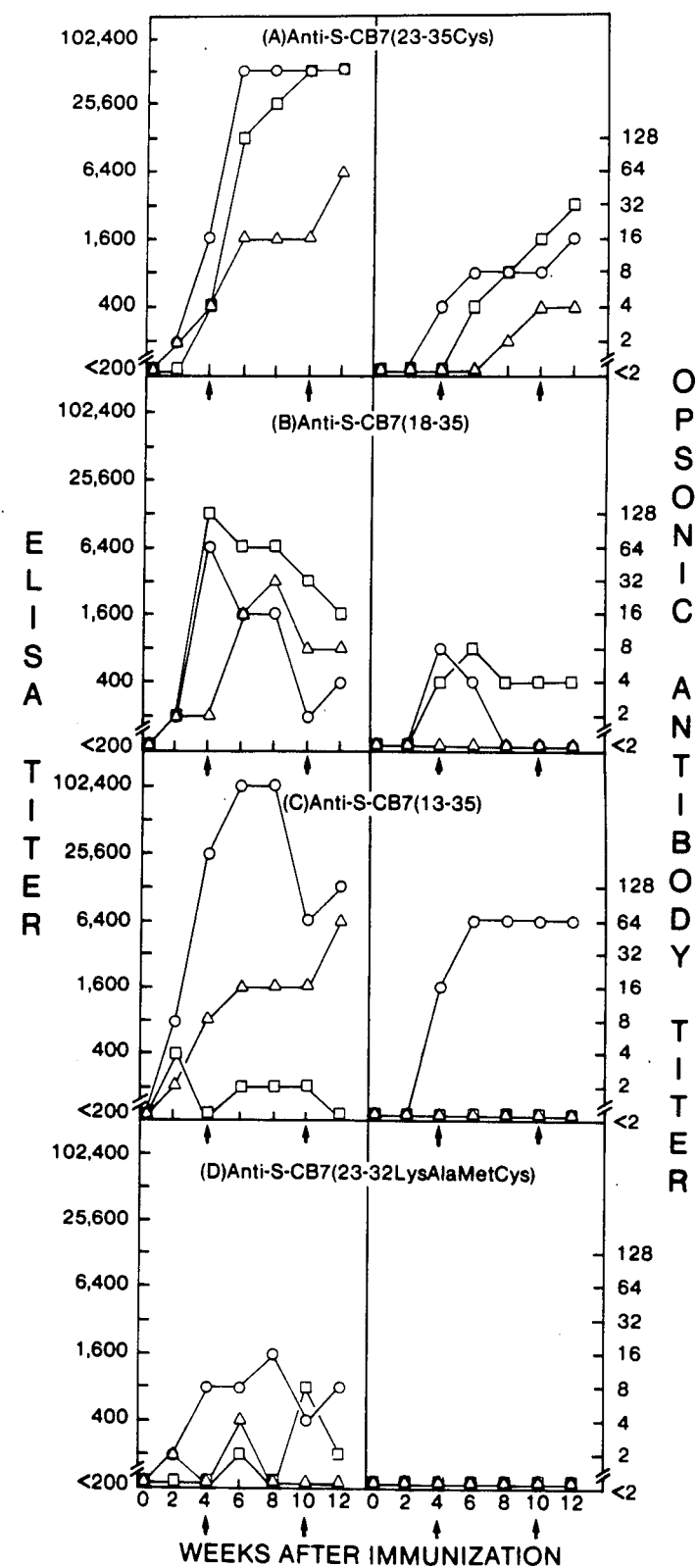
FIG. 1 shows immune responses in rabbits against tetanus toxoid conjugated synthetic peptide fragments of type 24 streptococcal M protein as measured by ELISA against pep M24 (left and opsonic antibody assays (right).

The mechanism whereby streptococcal infections give rise to complications such as rheumatic fever have remained, to a large extent, unexplained to date. Because the sera of some patients with rheumatic fever show serological cross-reactivity between heart tissue antigens and certain streptococcal antigens, it has been feared that immunization with intact M-protein vaccines may lead to rheumatic heart disease. See, for instance, Stollerman, *Rheumatic Fever and Streptococcal Infection*, supra. It has been observed that rabbits and mice immunized with cyanogen bromide fragments (CB6 or CB7) of type 24 M protein containing only 35 amino acid residues each developed opsonic and protective antibodies against type 24 streptococci.

The immunogenicity of small peptide fragments is encouraging for the development of safe and effective vaccines against those streptococcal infections that initiate rheumatic fever and rheumatic heart disease. The efficacy of very small peptides would permit disposal of a large portion of the M protein molecule and, therefore, should reduce the chances of eliciting immunological cross-reactions against host tissues. Thus, the continued identification of peptide structures responsible for protective immunity should yield a pool of small peptides that may eventually be synthesized and administered safely to humans as vaccine broadly protective against many serotypes of streptococci, particularly against those strains that trigger post streptococcal sequelae.

The protective antigenic determinants of type 24 group A streptococci appear to reside in repeating covalent structures of the M protein molecule. Each of seven distinct subpeptides derived by cleavage of a peptic extract of type 24 M protein (pep M24) with cyanogen bromide (CNBr) inhibit opsonic antibodies obtained from rabbits immunized with the uncleaved pep M24 molecule. The NH2-terminal sequences of two of these fragments, CB1 and CB2, are identical with each other and with the NH2-terminal sequence of the uncleaved pep M24 through at least the first 23 residues. The sequences of the remaining five peptides were entirely different from CB1 and CB2, but were identical with each other through the first 20 residues; thereafter, the sequences showed slight variability (Beachey, E.H., et al., Proc. Natl. Acad. Sci. USA 75, 3163-3167 (1978)).

When covalently linked to polylysine and emulsified in complete Freund's adjuvant, the subpeptides CB1, CB6 and CB7 have been shown to evoke type specific protective immune responses in laboratory animals (Beachey et al., J. Biol. Chem. 255, 6284–6289 (1980)). The complete covalent structures of CB6 and CB7 each contain 35 amino acid residues and their sequences are identical to each other except for three substitutions at positions 21, 24 and 26 (Beachey et al., J. Biol. Chem. 255, supra; U.S. Patent No. 4,284,537, issued August 18, 1981). Recently, a chemically synthesized peptide (S-CB7) identical to native CB7 except that the COOH-terminal residue of S-CB7 was methionine, not homoserine, was shown to evoke protective immune responses against challenge infections of mice with type 24 streptococci. In addition, it was found that one of the protective determinants resides in a peptide fragment of S-CB7 containing only 12 amino acid residues (Beachey et al., Nature 292, supra; U.S. Patent Application Ser. No. 402,355).

In accordance with the invention, small synthetic peptide fragments of *S. pyogenes* have been prepared and found to be immunogenic with respect to S. pyogenes.

As non-limiting examples of this invention there were prepared synthetic peptide fragments of CB7. The synthetic subpeptides include those labeled as S-CB7(24-35), S-CB7(23-35 Cys), S-CB7(18-35), S-CB7(13-35), S-CB7(8-35), S-CB7(23-34), S-CB7(13-34), S-CB7(6-34) and S-CB7(1-34).

These fragments contain an 11 amino acid sequence in common, the sequence of amino acids in the position 24 to 34 of CB7. The fragments may be defined by the following formula.

wherein:

X is defined as Lys-, Arg-Lys-, Ala-Ala-Leu-Ala-Ala-Arg-Lys-, Leu-Glu-Ala-Glu-Lys-Ala-Ala-Leu-Ala-Ala-Arg-Lys-, Ala-Lys-Ile-Lys-Thr-Leu-Glu-Ala-Glu-Lys-Ala-Ala-Leu-Ala-Ala-Arg- Lys-, Asp-Ser-Ala-Lys-Ile-Lys-Thr-Leu-Glu-Ala-Glu-Lys-Ala-Ala- Leu-Ala-Ala-Arg-Lys-, or Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-, and Y is -Ala, -Ala-Met, or -Ala-Met-Cys.

S-CB7(24-35) is identical to the carboxy terminal 12 residues of S-CB7. Its structure is:

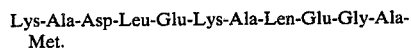

S-CB7(23-35 Cys) is identical to the carboxy terminal 13 residues of S-CB7 except that a cysteine residue has been added at the carboxy terminus. The sequence of the peptide therefore is:

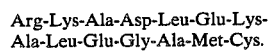

S-CB7(18-35) is identical to the carboxy terminal 18 residues of S-CB7. The amino acid sequence of S-CB7(18-35) is:

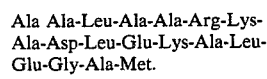

S-CB7(13-35) is identical to the carboxy terminal 23 residues of S-CB7. The amino acid sequence of S-CB7(13-35) is:

Leu-Glu-Ala-Glu-Lys-Ala-Ala-
   Leu-Ala-Ala-Arg-Lys-Ala-Asp-
   Leu-Glu-Lys-Ala-Leu-Glu-Gly-
   Ala-Met.

S-CB7(8-35) is identical to the carboxy terminal 28 residues of S-CB7. The amino acid sequence is:

Ala-Lys-Ile-Lys-Thr-Leu-Glu-
   Ala-Glu-Lys-Ala-Ala-Leu-Ala-
   Ala-Arg-Lys-Ala-Asp-Leu-Glu-
   Lys-Ala-Leu-Glu-Gly-Ala-Met.

S-CB7(23-34) is identical to the amino acid sequence of positions 23 to 34 of S-CB7. The amino acid sequence is:

Arg-Lys-Ala-Asp-Leu-Glu-Lys-
   Ala-Leu-Glu-Gly-Ala.

S-CB7(13-34) is identical to the amino acid sequence of positions 13 to 34 of S-CB7. The amino acid sequence is:

Leu-Glu-Ala-Glu-Lys-Ala-Ala-
   Leu-Ala-Ala-Arg-Lys-Ala-Asp-
   Leu-Glu-Lys-Ala-Leu-Glu-Gly-Ala.

S-CB7(6-34) is identical to the amino acid sequence of positions 6 to 34 of S-CB7. The amino acid sequence is:

Asp-Ser-Ala-Lys-Ile-Lys-Thr-
   Leu-Glu-Ala-Glu-Lys-Ala-Ala-
   Leu-Ala-Ala-Arg-Lys-Ala-Asp-
   Leu-Glu-Lys-Ala-Leu-Glu-Gly-Ala.

S-CB7(1-34) is identical to the amino acid sequence of positions 1 to 34 of S-CB7. The amino acid sequence is:

Asn-Phe-Ser-Thr-Ala-Asp-Ser-
   Ala-Lys-Ile-Lys-Thr-Leu-Glu-
   Ala-Glu-Lys-Ala-Ala-Leu-Ala-
   Ala-Arg-Lys-Ala-Asp-Leu-Glu-
   Lys-Ala-Leu-Glu-Gly-Ala.

In accordance with the invention, these synthetic fragments of S-CB7 were conjugated with a covalently linkable carrier. Each of the conjugates proved to be capable of producing immune responses as measured by opsonic antibody and ELISA tests. When covalently linked with glutaraldehyde to tetanus toxoid the conjugates evoked opsonic and protective antibodies in rabbits.

Furthermore, none of the conjugated synthetic peptides raised antibodies that were cross-reactive with human heart tissue.

In accordance with the invention, the carriers which are used to make the conjugate with the peptide sequences of the invention are any "natural" or synthetic carrier. The term carrier is a recognized term in the art and literature and sometimes is referred to as "coupler" or as "protein carrier." Numerous molecules, especially proteins and polysaccharides (in the mouse), may be coupled covalently to a hapten to act as a carrier. For this purpose, haptens may also be bound to erythrocytes, bacteriophages, artificial or synthetic macromolecules, and even to insoluble carriers. The hapten should possess one or several reactive groups that permit binding (covalent bonds) to carrier functional groups, under physicochemical conditions that maintain the integrity of the hapten structure, and as much as possible, of the carrier protein.

In some cases, binding of hapten to carrier requires mere contact (this is the case for nitrophenyl derivatives); most often, however, a coupling agent is required. When the hapten itself does not possess any reactive group, it may be introduced through a previous reaction. Thus, in order to couple steroids without carboxyl function to proteins, their alcohol function may be transformed into hemisuccinate, which introduces a carboxyl group.

Natural carriers used in accordance with the invention are known and are, typically, BSA or OVA. Synthetic carriers are, typically, polylysine. Hapten carriers are well known in the literature and need not be further described here to one skilled in the art. Generally, these carriers are covalently linked to the protein sequence.

Moreover, it has been found that the coupled antigen can be administered with a natural immunostimulant, preferably complete Freund's adjuvant or a synthetic immunostimulant, preferably of the MDP type, like MDP, its analogs and derivatives in aqueous saline solution, such as phosphate buffered saline ("PBS").

It is contemplated in accordance with the invention that whenever the term "MDP" is used for the synthetic immunostimulant, the term is and does include any synthetic immunostimulant which contains (or encompasses, or includes, etc.) the basic MDP (or the nor-MDP, i.e., 2-(2-acetamido-2-deoxy-D-glucos-3-0-yl-D-propionyl-L-alanyl-D-isoglutamine), structure, which structure has been recognized in the art to be the minimal structure to contribute to immunogenicity. The term "MDP immunostimulant", or "MDP type" or "nor-MDP type" or MDP analogs and derivatives are to be taken broadly. Such MDP immunostimulants are well known in the literature, which is incorporated by reference and include the following for illustrative purposes. U.S. Pat. Nos. 4,082,735, 4,082,736, 4,153,684, 4,220,637, 4,101,649, 4,186,194, 4,235,771, and the following publications: *Biken Journal,* Vol. 18, 105–111, 1975; *Microbiology* (1977) 388–394; *Cellular Immunology* 21, 243–249 (1976); *Proc. Natl. Acad. Sci. USA,* Vol. 73, No. 7, pps. 2472–2475, July 1976; *Int. J. Peptide Protein Res.,* 9, 1977, pps. 249–257; *Biken Journal,* Vol. 20, pps. 95–103, 1977; *C. R. Acad. Sci. Paris,* t. 285 (12 September 1977); *Prog. Allergy,* Vol. 25, pps. 63–105 (Karger, Basel 1978); and Cellular Immunology 35, pps. 173–179 (1978).

Figure 2:
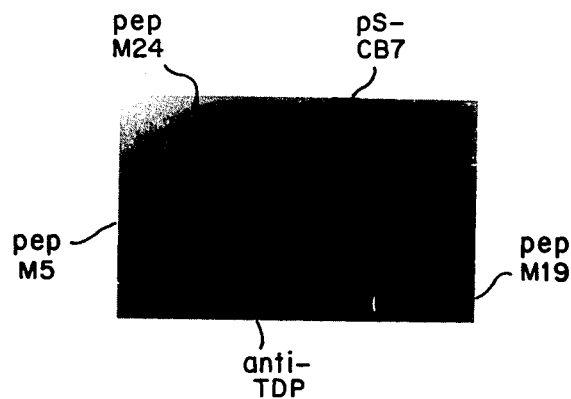
FIG. 2 shows double immunodiffusion in agar gel of anti-S-CB7(23-35Cys) (anti-TDP) against glutaraldehyde polymerized S-CB7(1-35) (pS-CB7) and the uncleaved natural proteins (pep M24, pep M5, pep M19).

When covalently linked with glutaraldehyde to tetanus toxoid (Example 3) S-CB7(23-35 Cys) evoked brisk opsonic and bactericidal antibodies in each of three immunized rabbits (FIGS. 1 and 2). None of the rabbits produced antibodies cross-reactive with heart tissue. Thus, this 14-residue subpeptide of CB7 is capable of raising protective antitype 24 antibody equally as well as the parent S-CB7.

Figure 3:
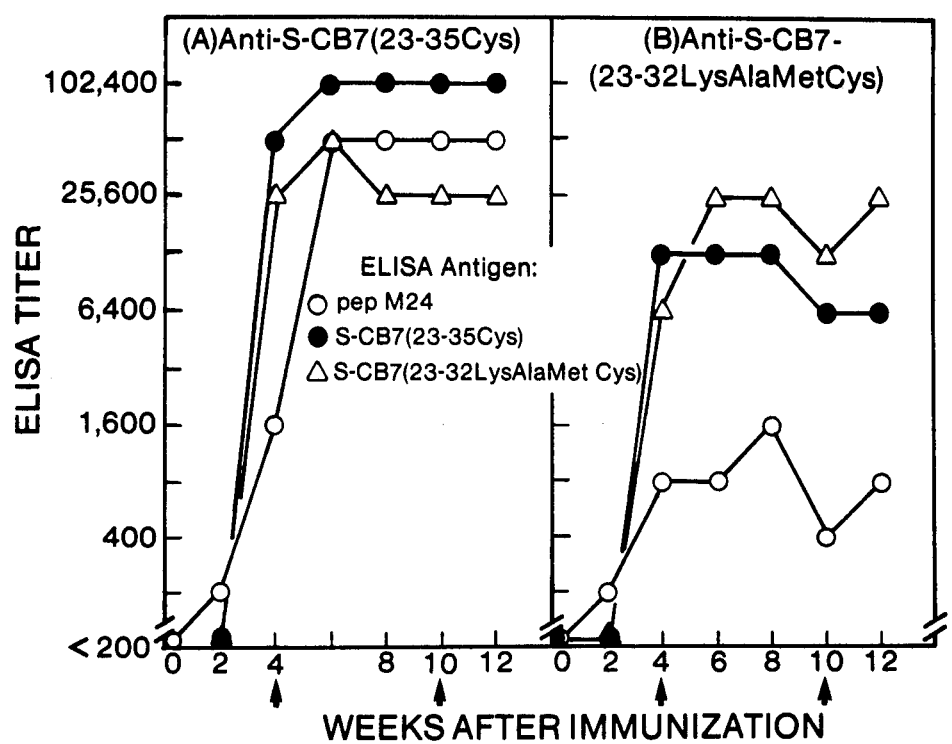
FIG. 3 shows ELISA of the interaction of (A) anti-S-CB7 (23-35Cys) and (B) anti-S-CB7(LysAlaMetCys) with pep M24 (○), S-CB7(23-35Cys) (●) S-CB7(23-32LysAlaMetCys) (△).

S-CB7(13-35) and S-CB7(18-35) were conjugated with glutaraldehyde to tetanus toxoid (Example 2). Each of three rabbits was injected with 100 g of the conjugated peptide emulsified in complete Freund's adjuvant. The rabbits were boosted with the same dose in phosphate-buffered saline at 4 weeks and 10 weeks after the initial injection. As can be seen by FIGS. 1 and 3, both peptides were capable of producing an immune response as measured by ELISA and opsonic antibody tests. None of the immune sera cross-reacted with frozen sections of human heart tissue.

Thus, the protective immunogenicity of chemically synthesized subpeptides of type 24 streptococcal M protein has been investigated. Copies of the COOH-terminal 13, 18 and 23 residues of cyanogen bromide fragment 7 (CB7) of pepsin extracted type 24 M protein (pep M24), except that the COOH-terminal residue was methionine instead of homoserine were synthesized. An additional residue of cysteine was added at the COOH-terminus of the tridecapeptide. In addition, an M protein fragment identical to the tridecapeptide except for a Lys/Gly substitution at position 33 was synthesized to study epitope specificity. Each of the peptides, designated S-CB7(13-35), S-CB7(18-35), S-CB7(23-35Cys) and S-CB7(23LysAlaMetCys), was conjugated to lysylated tetanus toxoid with glutaraldehyde and injected as an emmulsion in complete Freund's adjuvant into rabbits. Each of the conjugated peptides was capable of raising anti-pep M24 antibodies as measured by ELISA, although the lysine 33 substituted tridecapeptide was the least immunogenic failing to raise detectable opsonic antibodies. Each of the other peptide conjugates evoked type specific opsonic anti-streptococcal antibodies in at least one of three rabbits. The smallest peptide S-CB7(23-35Cys) was the most highly immunogenic raising opsonic antibodies in each of three immunized rabbits. A pool of the rabbit sera proved to be protective in mice challenged with type 24 streptococci. None of the antisera reacted with heterologous serotypes of M protein in ELISA or with heterologous whole streptococci in opsonophagocytic assays. Moreover, none reacted with frozen sections of human heart tissue in immunofluorescence assays. Analysis by ELISA and inhibition of ELISA indicated that S-CB7(23-35Cys) contains more than one epitope at least one of which is accessible in the natural protein. An additional epitope(s) was revealed by comparison of this peptide with peptide S-CB7(23-32LysAlaMetCys) containing a Lys/Gly substitution as position 33. The results indicate that a chemically synthesized peptide fragment representing as few as 13 residues of streptococcal M protein is capable of evoking protective anti-streptococcal antibodies without evoking heart cross-reactive antibodies.

S-CB7(1-34) conjugated to tetanus toxoid was capable of producing an immune response as measured by ELISA. The activity of the immune serum against the M24 protein is similar to that evoked by CB7(1-35). The serum also shows very good activity towards the peptide 1-34 itself (Table 1).

S-CB7 was polymerized with glutaraldehyde to form its respective homopolymer with a molecular weight from about 40,000 to 400,000 daltons. (Example 4). The homopolymer stimulates lymphocytes to divide but not to make cytotoxic cells.

The most intriguing finding was that under certain conditions a strong secondary response can be elicited with a polymerized synthetic antigen in the absence of either carrier or adjuvant. Furthermore, the immune response to the synthetic polymer was epitope specific in that the antibodies reacted most strongly and completely with the immunizing synthetic subpeptide. The weaker reactivity with the uncleaved parent M protein molecule suggests that certain epitopes exposed in the synthetic subpeptide are inaccessible for antibody reactivity in the intact parent molecule (Dale, et al., J. Exp. Med., 151, 1026 (1980). Nevertheless, a sufficient number of epitopes against which the poly-S-CB7 antibody was raised remained exposed in the intact M protein to allow the antibody to opsonize homologous M24 stretotococci. Interestingly, the epitope(s) against which the major portion of the anti-poly-CB7 antibody was directed appears to reside in the $NH_2$-terminal portion of S-CB7. As more of the $NH_2$-terminal end of the molecule was deleted, the less reactivity the subpeptides retained; the subpeptide encompassing the COOH terminal 12 residues of S-CB7 had virtually no reactivity. This observation is of particular interest in view of the prediction based on hydrophilicity profiles that this portion of the M Protein molecule encompasses a major antigenic determinant (Hopp. T.P. and Woods., K.R. Proc. Natl. Acad. Sci. USA, 78, 3823 (1981)).

These results further substantiate the idea that neither the whole M protein molecule nor even the whole CB7 peptide is needed for protective immunity against group A streptococci. These findings are important because this will enable the elimination of a large part of the molecule that may contain harmful determinants.

Other advantageous characteristics of the invention will appear from the examples which follow and with reference to FIGS. 1 to 3 illustrating the properties of the compounds of the invention.

EXAMPLE 1

Preparation of Streptococcal M Protein Peptides

Polypeptide fragments of M protein were isolated and purified from limited peptic digests of whole type 5, type 6 and type 24 *Streptococcus pyogenes* as previously described. (Beachey, et al., Infect. Immun., 9, 891 (1974); Beachey, et al., J. Exp. Med., 145, 1469 (1977); Beachey, et al., Proc. Natl. Acad. Sci. USA, 75, 3613 (1978)). The purified polypeptides designated pep M5, pep M6 and pep M24 were judged to be pure by sodium dodecyl-sulfate-gel electrophoresis and amino acid analyses. A polypeptide (S-CB7) identical to native CB7 of pep M24, except that the COOH-terminal homoserine was substituted with methionine, was synthesized by a solid phase method (Merrifield, J. Am. Chen. Soc., 85, 2149 (1963)) on a benzhydrylamine resin (Beckman). Cleavage of the synthetic peptides from this resin with hydrofluoric acid resulted in a carboxamide group at the COOH-terminus. After gel filtration (Biogel P6) and preparative reversed phase HPLC (Whatman Magnum 9 ODS), the peptide was judged to be homogeneous by analytical reversed phase HPLC and amino acid analysis. To obtain subpeptides of S-CB7, samples of the peptidyl resin were removed at various stages during the synthesis. Peptides S-CB7(1-35), (13-35) and (18-35) prepared in this way were chosen for the studies. In addition, two pep M24 peptides S-CB7(23-35Cys) and S-CB7(23-32LysAlaMetCys) were synthesized according to specifications by Penninsula Laboratories (San Carlos, CA). The crude, deblocked synthetic peptides were purified by reversed phase HPLC on Ultrasphere ODS2 (Whatman). The synthetic copies of pep M5 protein, S-M5(1-20) and S-M5(20-40) were used as control peptides.

EXAMPLE 2

Analytical Methods

Quantitative amino acid analyses were performed as described by Kang, Biochemistry, 11 1828 (1972). Samples were hydrolyzed in doubly distilled, constantly boiling HCl under $N_2$ for 24 h at 108° C. The hydrolyzed samples were then analyzed with a Beckman 232 automatic amino acid analyzer by a single column technique using a four-buffer elution system. No corrections were made for the loss of labile amino acids (threonine, serine, methionine and tyrosine) or the incomplete release of valine.

Automated Edman degradations were performed with a Beckman Sequenator (Model 890C) according to the principles first described by Edman and Begg (Eur. J. Biochem., 1, 80 (1967). The slow peptide-DMAA (071472) program of Beckman Instruments was used (Dixit, et al., Biochemistry, 14, 1933 (1975)). The phenylthiohedantoins were identified by HPLC (Zimmerman, et al., Biochem. Biophys. Res. Commun., 55, 1220 (1973)). Arginine . derivatives were identified as their parent amino acids after hydrolysis with 55% HI (Smithies, et al., Biochemistry, 10, 4912 (1971)). Repetitive yields of 97% were obtained during automated Edman degradation.

EXAMPLE 3

Conjugation of Synthetic Subpeptides with Tetanus Toxoid

Prior to conjugation to the peptides, the tetanus toxoid was first conjugated to L-lysine. To 0.8 µl of 10 mg/ml of tetanus toxoid there was added 1.0 ml of glutaraldehyde and the mixture was stirred for 1 hour at room temperature. L-lysine was added to a final concentration of 0.2 M and the mixture was stirred for 2 days at room temperature. The conjugate was washed 5-6 times with water by ultrafiltration using an Amicon flow cell equipped with a PM10 filter (Amicon Corp.). To 0.1 ml of 10 mg/ml of tetanus toxoid, there was added 0.9 ml of 0.1 M NaHCO$_3$ and 1.0 mg of synthetic peptide and the mixture was stirred for 1 hour at room temperature.

Then there was added 1 µl of glutaraldehyde and the mixture was stirred for 2 days at room temperature followed by the addition of 5 µl of glutaraldehyde. The mixture was then stirred for an additional 5 days. The conjugate was then washed 5 times with phosphate buffered saline (0.02 M phosphate, 0.15 M NaCl, pH 7.4) by ultrafiltration as described above. The conjugated peptides were stored frozen in 0.02M phosphate 0.15M NaCl, PH7.4 (PBS) at −70° C.

EXAMPLE 4

Polymerization of S-CB7

Polymerization of S-CB7 was achieved by treatment with glutaraldehyde under conditions described by Audibert, et al., Proc. Natl. Acad. Sci. USA 79, 5042 (1982).

EXAMPLE 5

Immunization of Rabbits

To determine the immunogenicity of the synthetic subpeptides, New Zealand white rabbits (2 kg) were injected subcutaneously with a 25 nmol dose of tetanus toxoid conjugated synthetic peptide emulsified in complete Freund's adjuvant. Rabbits were bled immediately before the immunizing injection and at 2-week intervals thereafter. At four and ten weeks, each rabbit was injected subcutaneously with a 25 nmol booster dose of the respective conjugated peptide in PBS, and sera were collected 2 weeks after each booster dose. Antisera against the pep M5, pep M6 amd pep M24 were prepared by similarly immunizing rabbits with 3 nmol doses of pep M24. All sera were stored at 4° C.

EXAMPLE 6

Immunization of Mice

Eight female Swiss mice (Iffa Credo, St-Germain-sur-L'Arbresle, France) per group were immunized subcutaneously. They received 10 ug of pep M24 either alone in phosphate-buffered saline (Pi/NaCl) or with 40 µg of alum or 100 ug of murabutide. Animals were boosted after 2 months with antigen alone; sera were collected separately at days 42 and 100. On day 115 and 205 the first group received a boost of monomeric or polymeric synthetic S-CB7 under the conditions described as follows:

The pep M24-PBS-treated mice were divided into two groups; 4 mice received no further treatment; the remaining 4 received an injection of monomeric S-CB7 on day 115 and of polymeric S-CB7 on day 205. Antibodies were measured on days 125 and 225.

EXAMPLE 7

Assays for Anti-M Protein Antibodies and M Protein Epitopes in Rabbit sera

The rabbit sera were assayed for anti-M protein antibodies by enzyme-linked immunosorbent assays (ELISA), immunoprecipitation tests in agar gels and opsonophagocytic antibody assays all as described by (Beachey et al., Proc. Natl., Acad. Sci. USA, 75, 3163 (1978) and (Beachey et al., J. Biol. Chem. 255, 6284 (1980)). The serotype specificity of the antibodies was determined by the capacity of the antisera to promote the phagocytosis of homologous and heterologous M serotypes of S. pyogenes. The presence of M protein epitopes on the synthetic subpeptides was assayed by the inhibition of ELISA and of the type specific opsonization of homologous M serotypes of S. pyogenes (Beachey et al., Nature, 292, 457 1981)). ELISA inhibition tests were performed by incubating a constant dilution of antiserum with serial dilutions of soluble synthetic peptide in PBS (Dale et al., J. Exp. Med., 151, 1026 (1980)). The mixtures were incubated at 37° C. for 30 min and then added to cuvettes coated with pep M5, pep M6, pep M19 or pep M24 (Beachey et al., J. Bio. Chem., supra).

In some experiments, the subpeptide S-CB7(23-35Cys) was covalently linked to bovine serum albumin (BSA) coated cuvettes via Cys through a bifunctional crosslinker, 3-(2-pyridyl-dithio) propionic acid N-hydroxysuccimide ester (Sigma). One mg of S-CB7 (23-35Cys) was dissolved in 0.5 ml 6M urea of ph 8.0 and reduced by adding dithiothreitol (45 mM, final concentration). The reduced peptide was freed of the reactants by passing it through a Sephadex G-10 column equilibriated with PBS. ELISA cuvettes were coated with BSA as described by Beachey et al., J. Biol. Chem., 225, 6284 (1980) and after washing the cuvettes to remove unattached protein, the albumin coating was first derivatized with the thiol crosslinker (see above) at 10 µg/ml for 30 min at ambient temperature. A solution containing the reduced peptide was then added to a final concentration of 5 µg/ml and allowed to react for 1 hr (the crosslinker reacts mostly with amino groups in BSA and then forms crosslinks with the peptide through its cysteine residue). After repeated washings with 0.15 M NaCl supplemented with 0.05% tween 20, ELISA were performed by the standard method (Dale, supra).

EXAMPLE 8

Immunofluorescence Tests

Each of the rabbit antisera was tested for immunologic cross-reactivity with human heart sarcolemmal membranes as previously described in detail by Dale and Beachey, J. Exp. Med., 156, 1165 (1982). Frozen sections of human heart tissue of sarcolemmal membrane sheaths prepared by the method of van de Rijn et al., J. Exp. Med., 146, 479 (1977) and dried and fixed on glass were reacted with immune rabbit serum followed by fluorescein-labeled goat anti-rabbit IgG and then examined by fluorescence microscopy (Beachey, 1977, supra). In control experiments, preimmune sera were substituted for the immune sera.

EXAMPLE 9

Titration of Antibodies in Mouse Sera

Sera were titrated using ELISA according to experimental conditions described by Audibert, 1982, supra. Microtiter plates (Nunc) were coated with pep M24 protein (0.4 µg/well) or S-CB7 peptide (2 µg/well) and incubated 2 hr at 37° C. After 2 washings, 200 µl of serial 10-fold dilutions of experimental sera were distributed in the wells and incubated for 1 hr at 37° C. After 5 washings, plates were incubated for 1 hr with peroxidase labelled goat anti-mouse IgG serum (Institut Pasteur Production). After extensive washing the substrate was added (O-phenylene-diamine (Sigma) 50 mg and $H_2O_2$ (35%) 20 µl in 100 ml of 0.05M citrate/phosphate buffer pH 5.

The reaction was allowed to proceed for 10 min with pep M24 and for 7 min with S-CB7 and then was stopped by the addition of 12.5% sulfuric acid. Absorbances were read at 492 nm in a Titerteck multiskan ELISA reader (Flow Laboratories). The negative control was a pool of normal mouse sera. Individual titers are expressed as the maximal dilution giving an absorbance twice as high as the negative control (generally about 0.2 O.D.). The inhibition studies were performed on sera diluted in BSA 1% at the level of $1\pm0.3$ O.D. when tested against pep M24 under the conditions described above.

The inhibiting antigens pep M24, monomeric S-CB7 or subpeptide fragments of S-CB7 were incubated with the immune sera at the concentration indicated. After 20 hr at 4° C. the sera were tested by the ELISA assay as described before.

Opsonophagocytic assays were performed as previously described using mixtures of lightly heparinized (10 U/ml) human blood, diluted suspensions of phagocytosis resistant streeptococci and either preimmune or immune test serums. (Example 7)

Automated Edman degradation confirmed the sequences of S-CB7 (13-35), S-CB7(18-35) and S-CB7(23-34Cys) to be identical to the corresponding regions of S-CB7(1-35) except that S-CB7 (23-35Cys) contained an additional residue of cysteine at the COOH-terminus (Table 2). The sequence of a fourth peptide identical to S-CB7(23-35Cys), except that the glycine residue at position 33 was substituted with lysine, also was confirmed by automated Edman degradation. The latter peptide is referred to as S-CB7(23-32LysAlaMetCys) and was employed to study the epitope specificity of the immune response to the unsubstituted peptide, S-CB7(23-35Cys). Each of the chemically synthesized peptides were covalently linked to tetanus toxoid with glutaraldehyde for use in the following studies of immunogenicity.

Previous studies have shown that S-CB7(1-35) covalently linked to polylysine is immunogenic in rabbits (Beachey, et al., Nature, 292, 457 (1981)). Because cleaved subpeptide fragments appeared to inhibit protective antibody, the capacity of shorter chain-lengths to elicite protective immunity was investigated. None of the synthetic subpeptides was found to be immunogenic in rabbits when injected subcutaneously in PBS or emulsified in Freund's complete adjuvant (CFA). When covalently linked to lysylated tetanus toxoid and emulsified in CFA, however, each of the peptides, except S-CB7(23-32LysAlaMetCys), elicited high titers of antibodies to the uncleaved pep M24 molecule as measured by ELISA in at least two of three immunized rabbits; one rabbit responded poorly to S-CB7(13-35) (FIG. 1). The tetradecapeptide S-CB7(23-35Cys) elicited responses equally as strong, if not stronger, than that of the longer peptides in each of three rabbits tested. This was especially true with respect to opsonic (protective) antibody assays. Thus, each of the three rabbits immunized with the shortest peptide, showed opsonic antibody responses, whereas only one of three rabbits immunized with S-CB7(13-35) and two of three rabbits immunized with S-CB7(18-35) showed such opsonic antibody responses. In contrast to the strong immune responses to S-CB7(23-35Cys), the same peptide with a single Lys/Gly substitution at position 33 evoked only weak or no responses as measured either by ELISA against pep M24 or by opsonophagocytic assays using type 24 streptococci (FIG. 1).

The antisera raised against each of the peptides formed immunoprecipitates with the uncleaved pep M24 molecule in agar gel diffusion test. Moreover, the antisera raised against even the smallest peptide produced precipitation lines of identity with glutaraldehyde polymerized S-CB7(1-35) and pep M24 (FIG. 2). None of the immune sera reacted in immunofluorescence tests with frozen sections of human heart tissue, and none reacted by ELISA against heterologous pep M5, pep M6 or pep M19 M proteins nor by opsonophagocytic assays with types 5, 6, or 19 streptococci (data not shown).

The activity of the antisera against S-CB7(23-35Cys) in opsonobactericidal and passive protection tests in mice challenged with the vaccine strain of type 24 group A streptococci was examined to identify the smallest region of the M protein molecule capable of stimulating protective antibody. As can be seen in Table 3, two of the three rabbit antisera against S-CB7(23-35Cys) obtained after two booster immunizations, killed all of the type 24 streptococci innoculated into fresh human blood. A pool of these two rabbit sera was capable of passively protecting mice challenged with type 24 streptococci (Table 4). These results indicate that a peptide containing as few as 13 M protein amino acid residues is capable of raising protective anti-streptococcal antibodies.

In order to determine the accessibility of the epitope(s) of S-CB7(23-35Cys), the capacity of the antibodies against this peptide to interact with the immunizing peptide, with the same peptide containing a lysine substitution at position 33 with the uncleaved pep M24 was examined by ELISA. The antibodies recognized the immunizing antigen the best but reacted in high titer with the natural pep M24 as well as with the lysine 33 substituted 23-35 subpeptide (FIG. 3A). In contrast, antibodies raised against the lysine 33 substituted peptide S-CB7 (23-3LysAlaMetCys) reacted the best with the substituted peptide but only poorly with the natural pep M24 (FIG. 3B). To further assess epitope specificity, homologous and heterologous peptides of various lengths were examined for their capacity to inhibit the interaction of anti-S-CB7(23-35Cys) with pep m24 or with S-CB7(23-35Cys) linked to BSA in ELISA. As can be seen in Table IV, when pep M24 peptide was used as the solid phase antigen each of the homologous type 24 peptide fragments, but not of the heterologous type 5 synthetic M protein fragments, was capable of inhibiting antibody binding to a high degree. Each of the peptides tested, except S-M5(1-20) and S-M5(20-40) inhibited binding by 100 % at a concentration of 10 uM. Each of the other subpeptides of S-CB7 were considerably less inhibitory at the same does, ranging between 40% and 47% inhibition. Interestingly, the uncleaved pep M24 molecule was the least inhibitory with 27% inhibition at 10 uM (Table 4). These results suggest that at least one epitope of S-CB7 (23-35Cys) is less accessible in the larger synthetic peptides and is least accessible in the unlceaved parent polypeptide.

Figure 4:
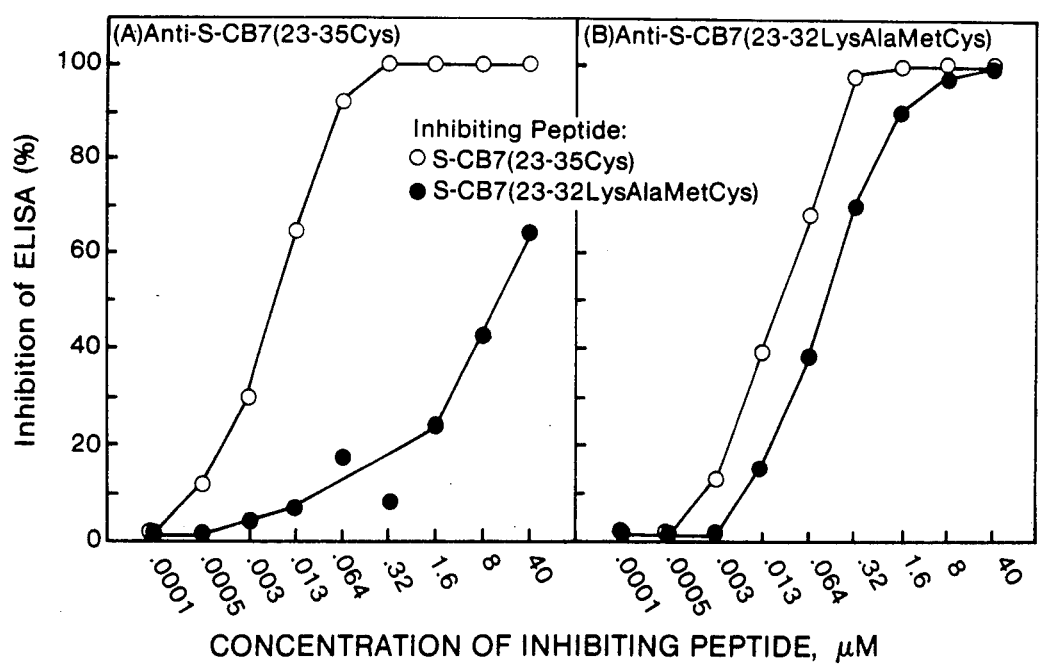
FIG. 4 shows ELISA of the inhibition of the interaction of (A) anti-S-CB7(23-35Cys) or (B) anti-S-CB7(23-32LysAlaMetCys) with pep M24 by S-CB7(23-35Cys) (○) or S-CB7(23-32LysAlaMetCys) (●).

To further assess the epitope specificity of the antibody response to S-CB7 (23-35Cys), the ability of this peptide and its lysine 33 substituted analogue to inhibit the ineractions of antisera to the respective peptides with the unleaved pap M24 molecule was compared. As can be seen in FIG. 4A, S-CB7 (23-35Cys) was a much better inhibitor than S-CB7(23-32LysAlaMetCys) of the interaction of anti-S-CB7(23-35Cys) with pep M24. In contrast, the two peptides showed similar patterns of the inhibition of the interaction of anti-S-CB7(23-32LysAlaMetCys) with the uncleaved M protein molecule, although interestingly, the unsubstituted peptide was consistently more inhibitory than the immunizing lysine 33 substituted peptide at all concentrations tested (FIG. 4B). These results indicate that the 13-residue COOH-terminal peptide of S-CB7 contains at least two distinct antigenic determinants (epitopes), one or more of which are protective and accessible for antibody interaction in the natural M protein molecule.

Three groups of mice received two injections of pep M24 with or without adjuvants as indicated in the legend of Table 5. Strong primary and secondary responses were observed in most mice treated with alum or murabutide (NAcMur-L-Ala-D-Gln-a-n-butyl-ester) as compared with their Pi/NaCl controls. The highest levels were observed in the glycopeptide-treated group on day 42 and especially on day 100. This marked enhancement was confirmed on day 25 when the experiment was terminated; the average titer of antibodies in the murabutide-treated group was 15,500 against pep M24 and 3,500 against S-CB7, whereas in the alum-treated group the antibody titers were respectively 240 against the protein and 100 against the synthetic peptide (data not shown). It should be noted that in all cases in the pep M24 immunized mice, the S-CB7 antibody titer was far lower than that against pep M24.

The pep M24-PBS-treated mice were divided into two groups: 4 mice received no further treatment; the remaining 4 received an injection of monomeric S-CB7 on day 115 and of polymerized S-CB7 on day 205. Antibodies were measured on days 125 and 225. On day 125 the antibody titers were similar in the sera of the two groups (average <160), but on day 225 the sera of the mice which had received the polymerized synthetic antigen had respectively titers of 37,000 - 35,000 - 4,500 and 3,100 of pep M24 antibodies (Table 6) and 45,000 - 40,000 - 8,000 and 4,500 of S-CB7 antibodies. In contrast, the antibody titers of the sera of the 4 control mice receiving only the pep M24 in Pi/NaCl remained low both against pep M24 and S-CB7 (average <200).

Pools of the 2 groups of sera were assayed in opsonophagocytic test. The pooled poly-S-CB7 immune serum showing an anti-pep M24 antibody titer of 12,800 by ELISA, prompted phagocytosis of type 24 streptococci by human neutrophils (50% of neutrophils associated with streptococci after 30 min of incubation with heparinized human blood) whereas the pep M24 in PBS immune serum showing an anti-pep M24 titer of 200 had no effect (no neutrophils associated with streptococci). The poly-S-CB7 serum also was shown not to react with frozen section of human heart tissue by immunofluorescence test performed as previously described in (Example 8).

The antibody specificity of the sera of the pep M24-Pi/NaCl-treated mice was analyzed before and after recall by the synthetic preparation (Table 7). Sera obtained after administration of pep M24 were completely inhibited by pep M24 but only partially by S-CB7. (It must be recalled that the structure of S-CB7 is repetitive along the 376 amino acids of the pep M24 molecule (Beachey, et al., Proc. Natl. Acad. Sci. U.S.A. 75 3163 (1978)).

In contrast, after the administration of the booster dose of polymerized S-CB7 the monomeric S-CB7 was completely inhibitory whereas pep M24 was only partially inhibitory, indicating that the recall was for antibodies directed against specific epitopes in S-CB7 and not against epitopes in the remaining pep M24 molecule not represented in S-CB7. It is also possible that some of the epitopes of S-CB7 are inaccessible in the uncleaved pep M24 (Dale, et al, J. Exp. Med., 151, 1026 (1980).

Figure 5:
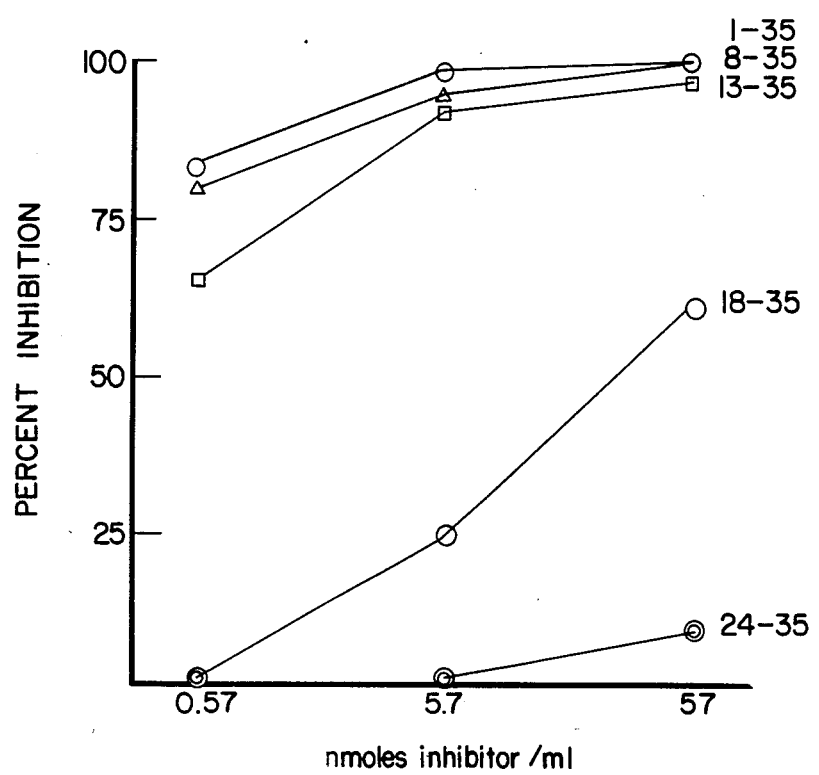
FIG. 5 shows inhibition of pep M24 antibodies in the serum of a poly-S-CB7-treated mouse by S-CB7 and its subpeptides.

A more precise analysis of specificity was performed on the serum showing the highest antibody titer after the booster dose of poymerized S-CB7. This peptide and four chemically synthesized subfragments consisting of the 12, 18, 24 or 28 COOH-terminal amino acid residues were incubated with the serum. The strongest inhibition was observed with S-CB7 and the 2 longer fragments (FIG. 5). These inhibition assays are not necessarily correlated with the immunogenicity of the shorter peptide fragments.

EXAMPLE 10

Synthesis of Synthetic Peptides

Peptides of the invention may be prepared in the following manner using the solid phase technique of Merrifield (J. Am. Chem. Soc., 85, 2149 (1963)).

The peptide chain is prepared starting from the C-terminal amino acid which is covalently attached by a benzylic ester linkage on chloromethylated styrene/divinylbenzene copolymer or by an amide linkage on benzhydrylamine resin. The succeeding amino acids, moving towards the N-terminal are added successively by repeating the cycle of operations shown in Table 8. The principal steps are as follows:

1. The deprotection of the group Boc (tertiobutyloxycarbonyl), used to protect alpha-amino functions, by using a solution of trifluoroacetic acid (TFA) in $CH_2Cl_2$.

2. The neutralization of alpha amine by means of a solution of diisopropylamine in $CH_2Cl_2$.

3. A coupling reaction accomplished by the activation of the carboxylic function of the amino acid by means of dicyclohexylcarbodiimide or the preparation of an active ester such as ortho-nitrophenyl. The coupling reagents are added in 3 to 6 times excess of the amount required to react with the active sites of the peptide attached to the resin. At the end of the coupling reaction, the absence of a free amine on the resin is verified by a test with ninhydrin. If there is a positive reaction for free amine, the coupling reaction is repeated.

In the course of the synthesis the reactive functions on the side chains of the amino acids are protected by the groups shown in Table 9.

At the end of the synthesis, the peptide is freed from the resin and the protecting groups are removed by treatment for 1 hour at 0° C. with a solution of hydrofluoric acid in anisole (9:1 V/V).

The peptides are then purified by gel filtration and then by ion-exchange chromatography or reverse phase partition chromatography.

The identity of the peptides is verified by amino acid analysis after acid hydrolysis and the homogeneity is checked by thin layer chromatography on silica gel in three different solvent systems as well as by reverse phase HPLC.

The peptides synthesized by this method include S-CB7(1-35), S-CB7(8-35), S-CB7(13-35), S-CB7(18-35), S-CB7(24-35), S-CB7(1-34), S-CB7(6-34), S-CB7(13-34) and S-CB7(23-34).

EXAMPLE 11

Demonstration of the Capacity of Peptides S-CB7(1-34) and S-CB7(23-34) To Induce Anti-Protein M24 Antibodies 1. Immunogenicity after coupling on tetanus toxoid.

The peptides are conjugated to the carrier by glutaraldehyde as described above. They are administered subcutaneously to 8 Wiss mice (8 per group) on days 1 and 30 at the dosage of 100 μg corresponding to 20 μg of the peptide and 80 μg of the carrier. On day 1 adjuvants were added to some groups as indicated in Table 10. It can be shown by this table that very high levels of antibodies recognizing not only the peptides but also the natural protein are obtained. Moreover, a very high level of opsonic activity was observed in the sera of mice immunized with the S-CB7(1-34) tetanus toxoid.

Tables 12 and 13 show the results obtained when the peptide is given as secondary immunization after primary immunization by the protein M24. It is interesting that these data correspond to a clinical situation since most people have a low degree of response to the natural protein. Here the antibody response is boosted with a synthetic peptide.

It is noteworthy that while earlier patents disclosing polymers of S. pyogenes teach that the peptides must be polymerized, it is apparent from these results that the peptides need not be polymerized.

2. Immunogenicity of the uncoupled peptide.

The peptide SCB7(1-34) has been shown to be capable of eliciting antibodies recognizing the natural protein M24 even when given free under certain conditions. These results are shown in Tables 11, 12 and 13. The date in Table 11 shows data that in FCA S-CB7(1-34) is immunogenic by itself. More interestingly, when given with murabutide in saline it can prime the animals, rendering them capable of showing a strong response to the natural protein M24 given as a secondary injection. It must be stressed that protein M24 given alone once at this dosage is not capable of evoking a measurable antibody response. The peptide was given at the dosage of 50 μg and the protein M24 at the dosage of 70 μg.

The invention also encompasses biologically active compositions comprising the antigen and an immunostimulant and wherein the antigen is administered with the immunostimulant. CFA is one such immunostimulant. Other natural and synthetic immunostimulants are well known in the art. The administration need not be concurrent; one may precede the other, in part or all of it. What is important is that the two components are present in the system of the mammal concurrently.

The biological compositions of the invention can be in any suitable form for administration to the mammal, whether a human or animal. Such are known in the art.

Solid compositions for oral administration include compressed tablets, pills, powders and granules. In such solid compositions, at least one of the active ingredients is admixed with at least one inert diluent such as starch, calcium carbonate, sucrose or lactose. These compositions may also contain additional substances other than inert diluents, e.g. lubricating agents, such as magnesium stearate, talc and the like.

Liquid compositions for oral administration include pharmaceutically-acceptable emulsions, solutions, suspensions, syrups and elixirs containing inert diluents commonly used in the art, such as water. According to the invention, the compounds for oral administration also include capsules of absorbable material, such as gelatin, containing said active component with or without the addition of diluents or excipients.

Preparations according to the invention for parenteral administration include sterile aqueous-organic, and organic solutions, suspensions and emulsions. Examples of organic solvents or suspending media are propylene glycol, polyethylene glycol, vegetable oils, such as olive oil, and injectable organic esters, such as ethyl oleate. These compositions can also contain adjuvants such as stabilising, preserving, wetting, emulsifying and dispersing agents. Aqueous compositions are by far preferred.

The percentages of active component in the said composition and method for causing the desired biological effect (e.g. immunological or hormonal inhibitory), can be varied so that a suitable dosage is obtained. The dosage administered to a particular patient is variable, depending upon the clinician's judgment using as the criteria: the route of administration, the duration of treatment, the size and condition of the patient, the potency of the active component, and the patient's response thereto. An effective dosage amount of active component can thus be determined best by the clinician considering all criteria and utilizing the best judgment on the patient's behalf. For practical considerations, the proportion may vary from about 0.01 to 20%, or higher, of active ingredient per composition. What is needed is that at least the minimum effective amount to give the desired effect be present.

Other aspects of the invention will readily become apparent to one skilled in the art.

TABLE 1

| Primary and Secondary Response | | |
|---|---|---|
| PRIMARY RESPONSE | DO 1/100 M 24 | PEPTIDE 1-34 |

TABLE 1-continued

Primary and Secondary Response

| | | | |
|---|---|---|---|
| FCA | Mouse 1 | 1.240 | 1.520 |
| | 2 | 0.845 | 0.420 |
| | 3 | 2 | 2 |
| | 4 | 1.630 | 2 |
| | 5 | 1.340 | 2 |
| | 6 | | 2 |
| Mean titer between 400 and 1,000 | | | |
| MDPG Bu | Mouse 1 | 0.310 | 0.750 |
| | 2 | 0.340 | 0.760 |
| | 3 | 0.845 | 1.740 |
| | 4 | 2 | 2 |
| | 5 | 1.475 | 1.650 |

| SECONDARY RESPONSE | $1.10^4$ | M 24 | PEPTIDE 1-34 |
|---|---|---|---|
| FCA | Mouse 1 | 0.300 | 0.250 |
| | 2 | 1.010 | 1.405 |
| | 3 | 0.480 | 0.650 |
| | 4 | 0.160 | 0.370 |
| | 5 | 0.520 | 0.740 |
| | 6 | 0.350 | 0.260 |
| MDPG Bu | Mouse 1 | 0.300 | 0.350 |
| | 2 | 0.245 | 0.325 |
| | 3 | 0.135 | 0.330 |
| | 4 | 0.305 | 0.370 |
| | 5 | 0.530 | 0.775 |
| Mean titer between 10,000 and 30,000 | | | |

TABLE 2

Automated Edman Degradation

| Synthetic Peptide | Amino Acid Sequence* |
|---|---|
| | 5      10     15     20     25     30     35 |
| S-CB7(1-35) | NFSTADSAKIKTLEAEKAALAARKADLEKALEGAM |
| S-CB7(13-35) | LEAEKAALAARKADLEKALEGAM |
| S-CB7(18-35) | AALAARKADLEKALEGAM |
| S-CB7(23-35Cys) | RKADLEKALEGAM C |
| S-CB7(23-32LysAlaMetCys) | RKADLEKALEKAM C |

*The single letter code for amino acid residues is used to conserve space and for ease of comparison. Underlined residues indicate substitutions or additions.

Key to the single letter code:

| N | Asn | A | Ala | L | Leu | C | Cys |
|---|---|---|---|---|---|---|---|
| F | Phe | D | Asp | E | Glu | R | Arg |
| S | Ser | K | Lys | G | Gly | | |
| T | Thr | I | Ile | M | Met | | |

TABLE 3

Indirect bactericidal Tests of Anti-tetradecapeptide S-CB7(23-35Cys) Against Type 24 S. Pyogenes
Number of colonies of type 24 streptococci after 3-h growth in test mixtures

| Rabbit Serum | Inoculum 42 | Inoculum 8 |
|---|---|---|
| Preimmune (Control)* | 2,000 | 892 |
| 8293 | 0 | 0 |
| 8294 | 1,248 | 148 |
| 8295 | 0 | 0 |

*The preimmune serum consisted of a pool of serum collected from each of the three rabbits before immunization with the tetradecapeptide.

TABLE 4

Protection by Anti-Tetradecapeptide Antibodies of Mice Challenged with Type 24 Streptococci

| Sera used to passively immunize mice | $LD_{50}$ in mice challenged with Type 24 streptoccoci |
|---|---|
| Preimmune | 500 (3/15)* |
| Anti-S-CB7(23-35Cys) | 400,000 (12/15) |

The numbers of survivors per number of mice challenged with type 24 streptococci.

TABLE 5

Capacity of Various Synthetic M Protein Peptides to Inhibit the Interaction of Anti-S-CB7(23-35Cys) With Pep M24 or the Homologous Peptide in ELISA

| Test Peptides | Concentration (nM) | Percent Inhibition of Interaction with: Pep M24 | S-CB7(23-35Cys)-BSA |
|---|---|---|---|
| Pep M24 | 0.3 | 42 | 0 |
| | 10.0 | 87 | 27 |
| S-CB7(1-35) | 0.3 | 77 | 0 |
| | 10.3 | 100 | 47 |
| S-CB7(13-35) | 0.3 | 80 | 10 |
| | 10.3 | 100 | 47 |
| S-CB7(18-35) | 0.3 | 77 | 10 |
| | 10.2 | 100 | 40 |
| S-CB7(23-35Cys) | 0.3 | 77 | 34 |
| | 10.0 | 100 | 100 |
| S-M5(1-20) | 0.3 | 0 | 0 |
| | 10.0 | 0 | 0 |
| S-M5(20-40) | 0.3 | 0 | 0 |
| | 10.0 | 0 | 0 |

TABLE 6

Anti-pep M24 and S-CB7 response of mice treated with pep M24 in Pi/NaCl, alum or murabutide.

| | Primary response (day 42) | | Secondary response (day 100) | |
|---|---|---|---|---|
| Treatment* | Anti-pep M24 | Anti-S-CB7 | Anti-pep M24 | Anti-S-CB7 |
| Pi/NaCl | 380-<100-<100-<100 <100-<100-<100-<100 (<135) | 110-<100-<100-<100 <100-<100-<100-<100 (<100) | 760-240-190-160 160-<100-<100-<100 (<225) | 380-<100-<100-<100 <100-<100-<100-<100 (<135) |
| Al(OH)₃ 40 μg | 6,800-5,000-1,600-490 260-220-130-110 (1,820) | 820-720-200-110 <100-<100-<100-<100 (<280) | 7,300-5,600-2,900-420 410-280-190 (2,440) | 3,000-750-300-100 <100-<100-<100 (<635) |
| Murabutide 100 μg⁻ | 10,000-6,200-5,600-3,300 3,300-2,700-1,200-300 | 2,800-1,100-1,100-1,000 430-300-300-150 | 22,000-21,000-16,500 11,000-8,400-2,950 | 5,600-4,800-3,000 2,300-1,400-500 |

TABLE 6-continued

Anti-pep M24 and S-CB7 response of mice treated with pep M24 in Pi/NaCl, alum or murabutide.

| Treatment* | Primary response (day 42) | | Secondary response (day 100) | |
|---|---|---|---|---|
| | Anti-pep M24 | Anti-S-CB7 | Anti-pep M24 | Anti-S-CB7 |
| | (4,075) | (900) | (13,640) | (2,900) |

*Eight mice per group received subcutaneously in 0.2 ml of Pi/NaCl 10 μg of pep M24 alone, with alum or with murabutide. After 2 months, they were boosted with 10 μg of antigen alone. Sera were taken separately on days 42 and 100.
†Antibodies were measured by ELISA titration. Individual titers and their arithmetic means are given. On day 42 the pep M24 and S-CB7 antibody responses of the murabutide-treated group were highly significantly different from the Pi/NaCl controls $P < 0.01$ as calculated by Student's t test. On day 100 the pep M24 antibody response of the murabutide-treated group was highly significantly different from the Pi/NaCl controls ($P < 0.001$) and from the alum-treated group ($P < 0.01$). The S-CB7 response of the latter group was significantly different from the Pi/NaCl group ($P < 0.01$).

TABLE 7

Inhibition by pep M24 or monomeric S-CB7 of the anti-pep M24 antibodies in sera of mice non-boosted and boosted with polymerized S-CB7.

| | | Day 100 (after 2 injections of pep M24) | | | Day 225 | | | | |
|---|---|---|---|---|---|---|---|---|---|
| | | | | | Not boosted with poly S-CB7 | | Boosted with poly S-CB7 | | |
| Inhibiting antigen | | (760) | (240) | (190) | (230) | (110) | (3,100) | (35,000) | (37,000) | (4,500) |
| pep M24 | 100 μg/ml | 100 | 100 | 100 | 84 | 72 | 89 | 43 | 65 | 43 |
| pep M24 | 10 μg/ml | 84 | 76 | 70 | 75 | 41 | 72 | 16 | 27 | 20 |
| pep M24 | 1 μg/ml | 65 | 48 | 40 | 59 | 11 | 48 | 0 | 0 | 0 |
| S-CB7 | 100 μg/ml | 48 | 48 | 23 | 0 | 29 | 100 | 100 | 100 | 80 |
| S-CB7 | 10 μg/ml | 0 | 0 | 0 | 0 | 20 | 97 | 45 | 92 | 44 |
| S-CB7 | 1 μg/ml | 0 | 0 | 0 | 0 | 0 | 80 | 15 | 63 | 24 |

Sera diluted in BSA 1% at the level of 1 ± 0.3 O.D. when tested against pep M24 under the conditions described in Materials and Methods.
Each column represents an individual serum. Figures between brackets indicate the titer of each of them. Results are given as the percentage of inhibition obtained with the competition at the concentrations indicated.

TABLE 8

Protocol of synthesis

| Reactants | Volume for 1 g of resin | Number of operations | Time |
|---|---|---|---|
| CH$_2$Cl$_2$ | 15 ml | × 3 | 2 mn |
| TFA—CH$_2$Cl$_2$ (⅔) | 13 ml | × 1 | 1 mn |
| TFA—CH$_2$Cl$_2$ (⅔) | 13 ml | × 1 | 30 mn |
| CH$_2$Cl$_2$ | 13 ml | × 5 | 2 mn |
| DIEA—CH$_2$Cl$_2$ (1/20) | 15 ml | × 3 | 2 mn |
| CH$_2$Cl$_2$ | 15 ml | × 5 | 2 mn |
| coupling | 15 ml | × 1 | 90 mn |
| CH$_2$Cl$_2$ | 15 ml | × 5 | 2 mn |

TABLE 9

Side chain protecting groups

```
                1           5              10
         Asn—Phe—Ser—Thr—Ala—Asp—Ser—Ala—Lys—Ile—
                          15                    20
         —Lys—Thr—Leu—Glu—Ala—Glu—Lys—Ala—Ala—Leu—
                          25                    30
         —Ala—Ala—Arg—Lys—Ala—Asp—Leu—Glu—Lys—Ala—
                                                35
                          —Leu—Glu—Gly—Ala—Met
```

| Amino acid | position | Protecting group |
|---|---|---|
| Ser | 3,7 | benzyl ether |
| Thr | 4,12 | benzyl ether |
| Asp | 6,26 | benzyl ester |
| Lys | 9,11,17,24,29 | benzyloxycarbonyl (Z) |
| Glu | 14,16,28,32 | benzyl ester |
| Arg | 23 | Tosyl |

TABLE 10

Immunogenicity of S-CB7 (1-34) and (23-34) after coupling on tetanus toxoid.

| GROUPS | ELISA TITERS* | | | | OPSONIC ANTIBODY TITERS |
|---|---|---|---|---|---|
| | ANTIPEPTIDE | | ANTI PROTEIN M24 | | |
| | Primary Response | Secondary Response | Primary Response | Secondary Response | Secondary Response |
| S-CB7(1-34)-TT + FCA | 500–2,000 (1,000) | 5,000–50,000 (400,000) | 200–1,000 (500) | 5,000–50,000 (20,000) | 80 |
| S-CB7(1-34)-TT + Murabutide | 500–1,000 (700) | 5,000–20,000 (15,000) | 100–500 (200) | 5,000–20,000 (7,500) | 80 |
| S-CB7(23-34)-TT + FCA | <100 | 100–1,000 (700) | <100 | 100–500 (200) | NT |
| S-CB7(23-34)-TT | <100 | 100–500 (400) | <100 | 100–500 (300) | NT |

*Titers are expressed as the maximal dilution giving an optical density (O.D.) three times higher than the O.D. obtained with prebleeding sera. Minimum and maximum titers in each group and the arithmetic mean are shown.

TABLE 11

Immunogenicity of the S-CB7 (1-34) when given uncoupled.

| PROTOCOL OF IMMUNIZATION | | | ELISA TITERS | | | |
|---|---|---|---|---|---|---|
| | | | ANTI PEPTIDE RESPONSE | | ANTI PROTEIN M24 RESPONSE | |
| Primary Day 1 | Secondary Day 27 | Tertiary Day 58 | Secondary* Day 34 | Tertiary Day 67 | Secondary Day 34 | Tertiary Day 67 |
| S-CB7(1-34) | S-CB7(1-34) | M-24 | <100 | 400 | <100 | 200 |
| S-CB7(1-34) + FCA | S-CB7(1-34) | M-24 | 50,000 | 200,000 | 10,000 | 30,000 |
| S-CB7(1-34) + Murabutide | S-CB7(1-34) | M-24 | <100 | 20,000 | <100 | 5,000 |

*Primary response is not given since very low titers were observed at this time.

TABLE 12

Immunogenicity of the S-CB7 (1-34) when given as a boost after immunization with protein M24.
(Primary Response)

| PROTOCOL OF IMMUNIZATION | | | ELISA TITERS | | | |
|---|---|---|---|---|---|---|
| | | | ANTI PEPTIDE RESPONSE | | ANTI PROTEIN M24 RESPONSE | |
| Primary Day 1 | Secondary Day 30 | Tertiary Day 60 | Secondary Day 37 | Tertiary Day 70 | Secondary Day 37 | Tertiary Day 70 |
| M24 | M24 | S-CB7 | 240 | 500 | 10,500 | 5,280 |
| M24 | M24 | S-CB7 | 240 | 9,150 | 10,500 | 22,680 |

TABLE 13

Immunogenicity of the S-CB7 (1-34) when given as a boost after immunization with protein M24.
(Secondary Response)

| PROTOCOL OF IMMUNIZATION | | | ELISA TITERS | | | |
|---|---|---|---|---|---|---|
| | | | ANTI PEPTIDE RESPONSE | | ANTI PROTEIN M24 RESPONSE | |
| Primary Day 1 | Secondary Day 30 | Tertiary Day 60 | Secondary Day 37 | Tertiary Day 70 | Secondary Day 37 | Tertiary Day 70 |
| — | M24 + murabutide | S-CB7 | <100 | 6,500 | 1,000 | 25,000 |
| | M24 + murabutide | — | <100 | <100 | 500 | 500 |

We claim:

1. A synthetic polypeptide which comprises the amino acid sequence

X-Ala-Asp-Leu-Glu-Lys-Ala-Leu-Glu-Gly-Y wherein X is Lys-, Arg-Lys-, Ala-Ala-Leu-Ala-Ala-Arg-Lys-, Leu-Glu-Ala-Glu-Lys-Ala-Ala-Leu-Ala-Ala-Arg-Lys-, Ala-Lys-Ile-Lys-Thr-Leu-Glu-Ala-Glu-Lys-Ala-Ala-Leu-Ala-Ala-Arg-Lys-, Asp-Ser-Ala-Lys-Ile-Lys-Thr-Leu-Glu-Ala-Glu-Lys-Ala-Ala-Leu-Ala-Ala-Arg-Lys-, or Asn-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys-; and Y is -Ala, -Ala-Met, or -Ala-Met-Cys.

2. The synthetic polypeptide of claim 1 which comprises the amino acid sequence

Arg-Lys-Ala-Asp-Leu-Glu-Lys-
Ala-Leu-Glu-Gly-Ala-Met-Cys.

3. The synthetic polypeptide of claim 1 which comprises the amino acid sequence

Ala-Ala-Leu-Ala-Ala-Arg-Lys-
Ala-Asp-Leu-Glu-Lys-Ala-Leu-
Glu-Gly-Ala-Met.

4. The synthetic polypeptide of claim 1 which comprises the amino acid sequence

Leu-Glu-Ala-Glu-Lys-Ala-Ala
Leu-Ala-Ala-Arg-Lys-Ala-Asp-
Leu-Glu-Lys-Ala-Leu-Glu-Gly-
Ala-Met.

5. The synthetic polypeptide of claim 1 which comprises the amino acid sequence

Ala-Lys-Ile-Lys-Thr-Leu-Glu-
Ala-Glu-Lys-Ala-Ala-Leu-Ala-
Ala-Arg-Lys-Ala-Asp-Leu-Glu-
Lys-Ala-Leu-Glu-Gly-Ala-Met.

6. The synthetic polypeptide of claim 1 which comprises the amino acid sequence

Arg-Lys-Ala-Asp-Leu-Glu-Lys-
Ala-Leu-Glu-Gly-Ala.

7. The synthetic polypeptide of claim 1 which comprises the amino acid sequence

Leu-Glu-Ala-Lys-Ala-Ala-
Leu-Ala-Ala-Arg-Lys-Ala-Asp-
Leu-Glu-Lys-Ala-Leu-Glu-Gly-
Ala.

8. The synthetic polypeptide of claim 1 which comprises the amino acid sequence

Asp-Ser-Ala-Lys-Ile-Lys-Thr-
Leu-Glu-Ala-Glu-Lys-Ala-Ala-
Leu-Ala-Ala-Arg-Lys-Ala-Asp-
Leu-Glu-Lys-Ala-Leu-Glu-Gly-
Ala.

9. The synthetic polypeptide of claim 1 which comprises the amino acid sequence

Asn-Phe-Ser-Thr-Ala-Asp-Ser-
Ala-Lys-Ile-Lys-Thr-Leu-Glu-

Ala-Glu-Lys-Ala-Ala-Leu-Ala-
Ala-Arg-Lys-Ala-Asp-Leu-Glu-
Lys-Ala-Leu-Glu-Gly-Ala.

10. The synthetic polypeptide of claim 1 which comprises the amino acid sequence Lys-Ala-Asp-Leu-Glu-Lys-
Ala-Leu-Glu-Gly-Ala-Met.

11. A synthetic antigen conjugate which comprises a polyvalent linkable carrier covalently linked to the polypeptide of claim 1 which antigen is able to elicit type-specific opsonic antibodies to *Streptococcus pyogenes* and which is not serologically cross-reactive with tissue antigens of the heart.

12. The synthetic antigen of claim 11 wherein the polyvalent linked carrier is a natural protein carrier.

13. The synthetic antigen of claim 12 wherein the carrier is tetanus toxoid.

14. The synthetic antigen of claim 11 wherein the carrier is a synthetic polymer.

15. The synthetic antigen of claim 14 wherein the carrier is a polylysine.

16. An immunogenic biological composition which comprises a biologically acceptable diluent, an immunostimulant and in an amount sufficient to elicit opsonic antibodies to *Streptococcus pyogenes* and not be serologically cross-reactive with tissue antigens of the heart, the synthetic antigen of claim 11.

17. The immunogenic biological composition of claim 16 wherein the immunostimulant is complete Freund's adjuvant or a synthetic immunostimulant.

18. A method for controlling streptococcal infections in a mammal which comprises administering to a mammal in a dose sufficient to control *Streptococcus pyogenes*, the composition of claim 16, and controlling *Streptococcus pyogenes* in said mammal.

19. A synthetic polypeptide which comprises the amino acid sequence

X-Ala-Asp-Leu-Glu-Lys-Ala-Leu-Glu-Gly-Y wherein X is

Lys-, Arg-Lys-, Ala-Ala-Leu-Ala-Ala-Arg-Lys-,
Leu-Glu-Ala-Glu-Lys-Ala-Ala-Leu-Ala-Ala-Arg-Lys-,
Ala-Lys-Ile-Lys-Thr-Leu-Glu-Ala-Glu-Lys-Ala-
Ala-Leu-Ala-Ala-Arg-Lys-,
Asp-Ser-Ala-Lys-Ile-Lys-Thr-Leu-Glu-Ala-Glu-
Lys-Ala-Ala-Leu-Ala-Ala-Arg-Lys-, or
Asn-Phe-Ser-Thr-Ala-Asp-Ser-Ala-Lys-Ile-Lys-
Thr-Leu-Glu-Ala-Glu-Lys-Ala-Ala-Leu-Ala-Ala-
Arg-Lys-; and y is -Ala, -Ala-Met, or
-Ala-Met-Cys, with the proviso that when X is Lys- or Ans-Phe-Ser-Thr-Ala-Asp-Ser-Ala-Lys-Ile-Lys-Thr-Leu-Glu-Ala-Glu-Lys-Ala-Ala-Leu-Ala-Ala-Arg-Lys, Y is not -Ala-Met.

20. The composition of claim 17 wherein the immunostimulant is MDP.

* * * * *